United States Patent [19]

Saeman

[11] 4,005,087
[45] Jan. 25, 1977

[54] SPRAY GRAINING TECHNIQUE FOR PREPARING GRANULAR HYDRATED ALKALI METAL DIHALOISOCYANURATE

[75] Inventor: Walter C. Saeman, Cleveland, Tenn.

[73] Assignee: Olin Corporation, New Haven, Conn.

[22] Filed: Sept. 29, 1975

[21] Appl. No.: 617,879

[52] U.S. Cl. .................................... 260/248 C
[51] Int. Cl.² ................................. C07D 251/36
[58] Field of Search ........................ 260/248 C

[56] References Cited
UNITED STATES PATENTS 3,853,867  12/1974  Berkowitz ..................... 260/248

Primary Examiner—John M. Ford
Attorney, Agent, or Firm—Donald F. Clements; James B. Haglind; Thomas P. O'Day

[57] ABSTRACT

Granular alkali metal dihaloisocyanurate particles (such as sodium dichloroisocyanurate) comprised of a core of alkali metal dihaloisocyanurate encapsulated in a plurality of layers of hydrated alkali metal dihaloisocyanurate are produced by spraying a pumpable and sprayable aqueous slurry of hydrated alkali metal dihaloisocyanurate particles onto suspended particles of solid alkali metal dihaloisocyanurate in anhydrous or hydrated form above a moving bed of said particles. The solid particles coated with the slurry are heated to simultaneously evaporate and remove water from the slurry whereby said particles are coated with a layer of solid hydrated alkali metal dihaloisocyanurate.

A portion of the moving bed of coated particles is removed from the spraying zone and further processed, if desired. In one embodiment, the hydrated particles are sized, and undersize and crushed oversize are recycled to the moving bed. In another embodiment, the coated particles, with or without sizing, are dried to produce granular particles having the desired moisture content or degree of hydration.

The resulting coated or layered granular particles of hydrated alkali metal dihaloisocyanurate have a high level of integrity and resist degradation and dusting when subjected to rather severe handling conditions. In addition, the novel granular hydrated alkali metal dihaloisocyanurate particles of this invention are highly stable when contacted with lighted cigarettes, organic materials and the like.

26 Claims, 3 Drawing Figures

SPRAY GRAINING TECHNIQUE FOR PREPARING GRANULAR HYDRATED ALKALI METAL DIHALOISOCYANURATE

This invention relates to granular alkali metal dihaloisocyanurate particles which resist dusting and degradation during handling, and which are highly stable when contacted with lighted cigarettes or organic materials.

In most methods for the commercial manufacture of alkali metal dihaloisocyanurates, such as sodium dichloroisocyanurate and potassium dichloroisocyanurate, a slurry containing crystals of alkali metal dihaloisocyanurate dihydrate in an aqueous solution is formed from a variety of selected reactants and the resulting slurry is filtered to produce a wet cake of alkali metal dihaloisocyanurate.

U.S. Pat. No. 3,035,057, which issued May 15, 1962, to Symes et al. discloses a process for preparing alkali metal dihaloisocyanurate by reacting trichloroisocyanuric acid with a trialkali metal isocyanurate to form a slurry of alkali metal dihaloisocyanurate dihydrate. The solid particles are separated and heated to dryness in vacuo at a temperature of about 30° C. to form particles of the dihydrate, at about 70° C. to form particles of the monohydrate and at about 110° C. to form particles of anhydrous alkali metal dihaloisocyanurate. Mixtures of these products are also disclosed. It is difficult by this technique to control the particle size of the dried crystalline product, and as a result, the relatively large portion of finely divided particles that are produced must be agglomerated by compression or otherwise processed before they are useful in sanitizing processes and the like.

U.S. Pat. No. 3,289,319, which issued Dec. 6, 1966, to Wenzke et al., discloses a process for preparing sodium dichloroisocyanurate by reacting cyanuric acid with caustic and chlorine to form dichlorocyanuric acid, and reacting the resulting product with additional caustic to form sodium dichloroisocyanurate. The resulting wet cake is then admixed with previously dried sodium chloroisocyanurate in a pug mill or other apparatus provided with a beating means to form a feed for a dryer which is also provided with beating means. Although this technique of mixing wet cake with dry material prevents caking in the dryer, particularly when the beating means is utilized, a large quantity of recycled dry product is required to carry out the process, which reduces the capacity of the apparatus. In addition, a relatively large portion of finely divided particles are formed because there is little control over the particle size of the dry product.

U.S. Pat. No. 3,818,002, which issued June 18, 1974, to Goelz et al. describes a process for preparing anhydrous sodium dichloroisocyanurate in a fluidized bed where an aqueous solution or suspension of sodium dichloroisocyanurate is sprayed on to a fluidized bed of finely divided particles of anhydrous sodium dichloroisocyanurate, wherein the drying gas is at a temperature from 100° to 300° C to reduce the moisture content to near zero percent and to process particles of anhydrous sodium dichloroisocyanurate. In addition to being limited to preparing anhydrous sodium dichloroisocyanurate by this technique, other problems encountered are the poor thermal efficiency and the large amount of finely divided particles produced by abrasion of the suspended particles in the fluidized bed.

Another disadvantage of processes available previously for drying wet cakes of alkali metal dihaloisocyanurate is that extremely high temperatures are required to obtain the desired degree of drying, and these high temperatures also cause a substantial loss of available chlorine in the product.

There is a need in the industry at the present time to have an improved process for preparing and drying solid alkali metal dihaloisocyanurate particles in which the proportion of finely divided particles is substantially reduced and the loss of available chlorine is minimized.

It is a primary object of the present invention to provide an improved process for preparing alkali metal dihaloisocyanurate particles, in which control of particle size, control of available chlorine content and control of moisture content of the particles is achieved.

It is a further object of this invention to provide an improved process for preparing sodium dichloroisocyanurate particles, in which control of particle size, control of available chlorine content and control of moisture content of the particles is achieved.

It is another object of the invention to provide a method for producing particulate alkali metal dihaloisocyanurate from an aqueous slurry thereof at relatively low reaction and drying temperatures to minimize losses of available chlorine caused by decomposition during processing.

It is still a further object of this invention to provide a method for preparing smooth-surfaced, rounded, granular alkali metal haloisocyanurate particles free of fragile edges which are subject to abrasion and dust formation during handling.

A further object of this invention is to provide a method for preparing smooth-surfaced, rounded, granular sodium chloroisocyanurate particles free of fragile edges which are subject to abrasion and dust formation during handling.

It is a further object of this invention to provide novel alkali metal dihaloisocyanurate particles having an inner core or portion of alkali metal dihaloisocyanurate and an outer portion of a different hydrate of the same or different alkali metal dihaloisocyanurate having a different moisture content than the inner portion, and a process for producing them.

Still a further object of this invention is to provide novel sodium chloroisocyanurate particles having an inner core or portion of sodium dichloroisocyanurate and an outer portion of a different hydrate of sodium dichloroisocyanurate having a different moisture content than the inner portion, and a process for producing them.

These and other objects of this invention will be apparent from the following detailed description of the invention.

The novel composition of this invention is smooth surfaced, rounded, granular alkali metal dihaloisocyanurate particles, wherein each particle is comprised of a core of alkali metal dihaloisocyanurate encompassed with a plurality of rounded layers of hydrated alkali metal dihaloisocyanurate, wherein the core of each particle generally has a diameter which ranges from about 200 to about 2,000 microns and the novel coated granule has a diameter ranging from about 400 to about 5,000 microns.

The novel rounded granules of this invention are formed in the method of this invention from a pumpable and sprayable aqueous slurry of hydrated alkali metal dihaloisocyanurate in a process which comprises:
a. maintaining a moving bed of solid alkali metal dihaloisocyanurate in the lower part of a distributing zone having an upper part and a lower part,
b. lifting a portion of the moving bed of particles to the upper part of the distributing zone and releasing the lifted particles to fall downwardly through the upper portion of the distributing zone to said moving bed in the lower portion thereof,
c. spraying onto said falling particles a pumpable and sprayable aqueous slurry of hydrated alkali metal dihaloisocyanurate
d. maintaining a temperature in said distributing zone sufficiently high to simultaneously evaporate and remove water from the slurry on said falling particles, whereby the resulting particles after water removal are coated with a layer of solid hydrated alkali metal dihaloisocyanurate and,
e. removing at least a portion of the resulting coated solid hydrated alkali metal dihaloisocyanurate particles from the distributing zone.

Lack of cohesiveness between crystals of hydrated alkali metal dihaloisocyanurate is counteracted in the structure and growth of the novel granular product of this invention in that freshly deposited, pliable moist layers of new isocyanurate solids are packed and pounded onto the dried hardened underlying seed substrate by innumerable impacts and the grains cascade in the rotary drum or are otherwise forced into violent collision with one another. Where crystalline particles are too large to submit to hardening by collision impact, these may retain individual identity as nuclei to seed the bed or they may be conveyed out of the bed by entrainment in the air flow through the rotary drum and collected in a dry dust collector, pulverized and returned in more finely divided form, more susceptible to cohesion and hardening by collision impact.

If desired, the coated particles removed from the distributing zone can be further dried to reduce the water content to a lower level. Sizing of all or a portion of the coated alkali metal dihaloisocyanurate particles separated from the distributing zone can be accomplished prior or subsequent to drying or other treatment.

The novel rounded granular alkali metal dihaloisocyanurate particles prepared in accordance with the process of this invention have a high level of integrity and resist dusting and degradation when subjected to severe handling conditions. For example, irregularly shaped granules of commercial alkali metal dihaloisocyanurate break easily along the thin fragile edges when subjected to pressure and abrasion. The fragmented edges form fine dust which is easily dispersed in ambient atmosphere and results in severe respiratory irritation, discomfort and health hazards. Fragile edges are absent on the novel rounded grain of this invention and hence dusting cannot occur. Even if this novel grain fractures under pressure, fragments remain sufficiently large to escape entrainment in ambient air during normal handling of the product. As a result, even though the novel alkali metal dihaloisocyanurate particles of this invention may be fractured under severe handling conditions during shipment, nevertheless, a minimum of finely divided particles are formed. Also, as a result, a more uniform distribution of the alkali metal dihaloisocyanurate in the water being treated can be obtained and respiratory irritation and discomfort from entrained isocyanurate dust in air is greatly minimized. In addition, when the proper level of moisture content is obtained, there is a high degree of resistance to ignition by lighted cigarettes or the reaction caused when contacted with organic materials.

Figure 1:
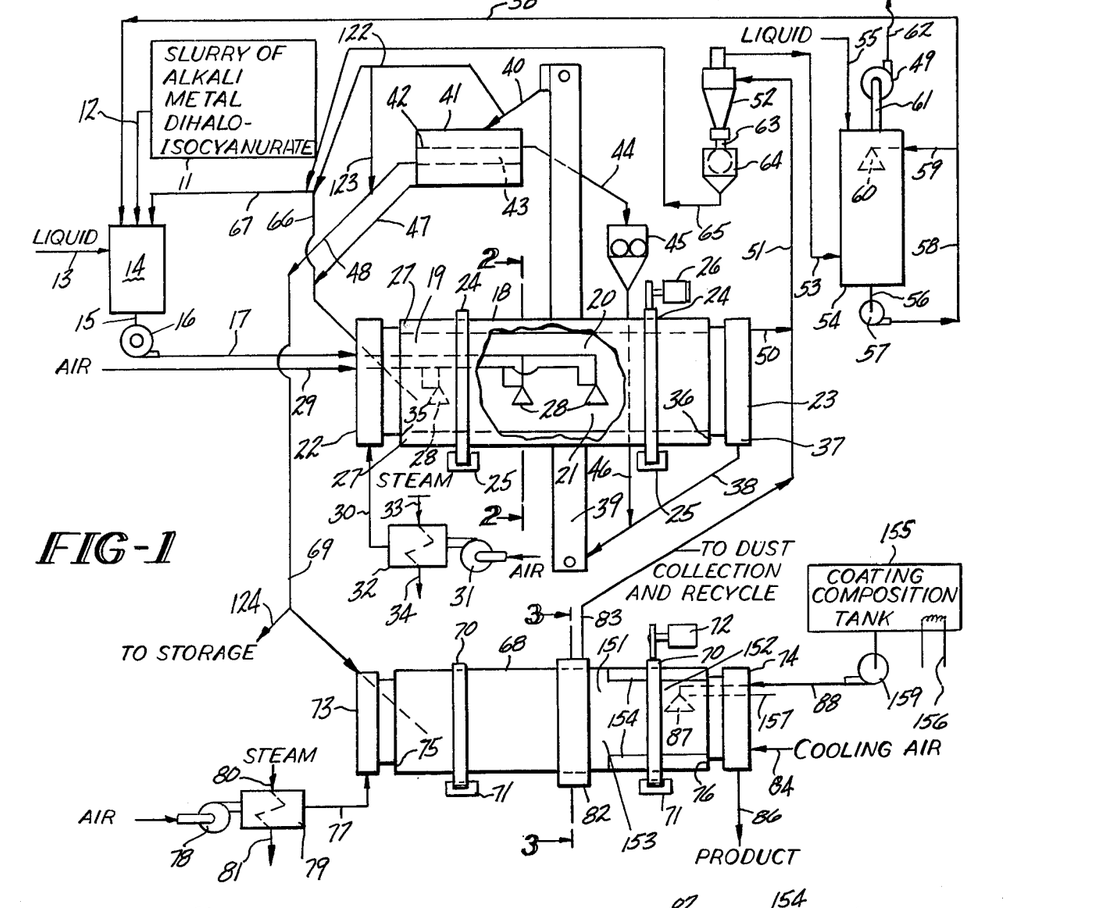
FIG. 1 shows an embodiment of the invention which utilizes a spray grainer as a distributing zone, with recycle of fines and crushed oversize to the moving bed. The product fraction is conveyed to a separate dryer where the water content is reduced to the desired level.

More in detail, as shown in FIG. 1 an alkali metal dihaloisocyanurate process slurry of the type formed in a commercial process such as described in the above patents may be conveyed to an agitated slurry storage tank 11 where it is stored until ready for use in the process. The slurry is conveyed through slurry storage line 12 and, if necessary, is admixed with a liquid such as water fed through liquid line 13 into make-up slurry mixer 14 to produce a pumpable and sprayable slurry of alkali metal dihaloisocyanurate. Other components may be added to slurry mixer 14, as discussed below. This slurry is conveyed from make-up slurry mixer 14 through mixer discharge line 15 by means of slurry pump 16 through slurry feed line 17 to spray grainer 18.

Spray grainer 18 has a distributing zone 19 with an upper portion 20 and a lower portion 21, a feed end 22 and an opposite discharge end 23. Spray grainer 18 is provided with exterior tires 24 secured to the exterior thereof which are adapted to rotate in trunnions 25, exterior tires 24 being driven by a suitable motor driven rotation means 26 to effect rotation of spray grainer 18 within the desired speed range.

Figure 2:
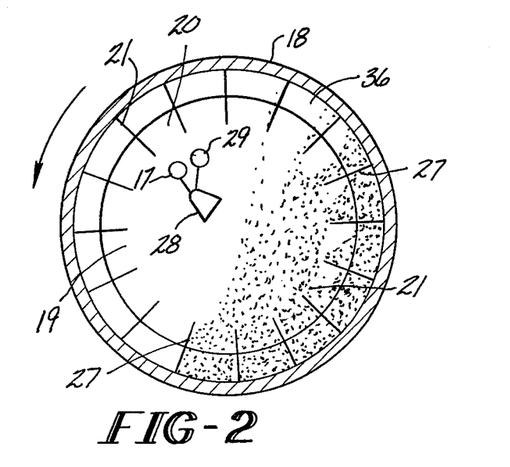
FIG. 2 is a cross-sectional view of the spray grainer of FIG. 1 through the lines 2—2 of FIG. 1.

As shown in FIG. 2, a bed of solid alkali metal dihaloisocyanurate particles is placed in lower portion 21 of distributing zone 19 to form, when spray grainer 18 is rotated, a moving bed of particulate solids which gradually progresses from feed end 22 to discharge end 23 of spray grainer 18. Transport of the feed from the feed end to the discharge end can be solely by interaction with a co-current flow of drying gases (as described below) or by a combination of gas induced transport aided or retarded by positive or negative slope of the drum axis. Bed transport can also be aided or detained by use of inclined vanes and dam rings attached to the interior of the drum wall.

As shown further in FIG. 2, a series of lifters 27 are positioned around the interior circumference of spray grainer 18 to lift the particles of alkali metal dihaloisocyanurate from the moving bed in lower portion 21 to the upper portion 20 of distributing zone 19. As spray grainer 18 rotates, the particles gradually fall from lifters 27 as they approach the top of upper portion 20 and fall through distributing zone 19 to lower portion 21 into the moving bed of solid particles. While the solid particles are falling from lifters 27 from upper portion 20 to lower portion 21 of distributing zone 19, slurry pump 16 is continuously conveying through slurry feed line 17 the pumpable and sparyable slurry of alkali metal dihaloisocyanurate to a plurality of spray nozzles 28. Compressed air or gas is conveyed through compressed air or gas feed line 29 to nozzles 28 in order to disperse the slurry as fine droplets from the spray nozzles and to effect the spraying of these fine droplets of slurry onto the falling particles of alkali metal dihaloisocyanurate.

Heated air or other inert gas contacts the alkali metal dihaloisocyanurate particles wetted with the slurry to simultaneously evaporate and remove water and to deposit a thin solid layer of the hydrated alkali metal dihaloisocyanurate component of the slurry on the surface of the wetted particles. The coated particles fall to the moving bed and continue to be lifted, dropped and coated until they are discharged from spray grainer 18. Any convenient heating technique may be employed. For example, heated air is preferably conveyed through heated air line 30, co-current with the flow of the moving bed of solids. Air is conveyed by blower 31 to heat exchanger 32 which is heated by steam conveyed through steam feed line 33 to heat exhanger 32. The heat air produced in heat exchanger 32 is conveyed through heated air line 30 by blower 31 into feed end 22 through spray grainer 18, and passed out discharge end 23. The heated air fed to spray grainer 18 is generally at a temperature in the range from about 75° C. to about 250° C. to effect simultaneous evaporation and removal of water from the falling particles. The steam condensate from heat exchanger 32 is discharged through steam discharge line 34.

At feed end 22 a feed retaining flange 35 is secured to the interior wall of spray grainer 18 in order to retain the moving bed of particles within spray grainer 18. Similarly, at discharge end 23, a discharge retaining flange 36 is secured to the interior wall of spray grainer 18 in order to retain most of the moving bed of particles within spray grainer 18. Feed retaining flange 35 and discharge retaining flange 36 each have an opening in the center, preferably of circular shape. The diameter of the opening in discharge retaining flange 36 is preferably greater than the diameter of the opening of feed retaining flange 35 in order to insure that particles are discharged from spray grainer 18 at discharge end 23 rather than at feed end 22. For co-current air flow, bed transport is primarily by interaction of the cascading bed with the air stream. Positive or negative axial slope can be used to aid or retard air transport. Also, internal dam rings (not shown) can be used to retard flow by increasing bed depth. Also, slanted vanes (not shown) can be mounted to inner walls of spray grainer 18 to aid or retard bed transport.

As the number and size of alkali metal dihaloisocyanurate granules increases, the moving bed builds up behind discharge retaining flange 36 until a level is reached where the particles fall out through the opening in discharge retaining flange 36 into solids collection zone 37. Granules from solids collection zone 37 are conveyed by suitable conveying means to a suitable size classification apparatus. For example, a solids conveying means such as a chute 38, elevator 39 and inclined trough 40 convey all or part of the solids to screens 41 which are preferably heated to minimize blinding. However, other apparatus such as an air classifier may be used to separate the particles into an over-size fraction, an under-size fraction and a product fraction. Screens 41 contain an over-size screen 42 and an under-size screen 43 which separate over-size particles and under-size particles from the product fraction. Generally, any desired particle size can be obtained. In a typical separation, the over-size screen 42 has a mesh size in the range from about 4 to about 16 mesh and the under-size screen 43 has a mesh size in the range from about 20 to about 60 mesh. Under-size screen 43 always has a mesh opening smaller than over-size screen 42. A typical product fraction ranges from about 14 to about 30 mesh, but size range can be varied as desired. Over-sized particles retained by over-size screen 42 ae conveyed through over-size particle conduit 44 to roll crusher 45 where the over-size particles are crushed to pass through over-size screen 42 and then conveyed through crushed over-size particle conduit 46 to chute 38 where the crushed particles are recycled through elevator 39 to screens 41. Under-size particles which pass through under-size screen 43 are conveyed by means of under-size particle conduit 47 to the feed end of spray grainer 18, where they serve as core particles or nuclei for the formation of additional granules of alkali metal dihaloisocyanurate. A product fraction of rounded granular alkali metal dihaloisocyanurate is collected in product conduit 48 and processed as described more fully below.

Exhaust fan 49 is used to withdraw moist air having finely divided particles of alkali metal dihaloisocyanurate suspended therein from solids collection zone 37 through a series of conduits and apparatus. The solid-laden moist air is withdrawn from solids collection zone 37 through conduit 50 to dust collector feed line 51 and into dry dust collector 52, preferably of the cyclone type. Air exhausted from the top of dry dust collector 52 is conveyed through air discharge line 53 to wet scrubber 54 for more effectual cleaning. Liquid such as water or a dilute alkali metal dihaloisocyanurate solution which may be produced as a by-product in the preparation of the alkali metal dihaloisocyanurate slurry is fed through liquid feed line 55 to the top of wet scrubber 54 where it contacts the moist air and removes the bulk of fine solid particles retained in the air. The resulting dust laden slurry is removed from the bottom of scrubber 54 through slurry discharge line 56 by means of scrubber pump 57. A portion of slurry discharge from scrubber pump 57 is conveyed to make-up slurry mixer 14 through slurry recycle line 58. The remainder of the slurry from slurry recycle line 58 is recycled to the top of scrubber 54 through slurry recycle line 59 and then sprayed through scrubber nozzle 60 onto the rising dust laden air fed into the bottom of wet scrubber 54. Contact between the slurry and air removes substantially all of the suspended solids from the air. The resulting gases depleted of dust are conveyed through exhaust conduit 61 and exhaust fan 49, and discharged through air exhaust line 62 into the atmosphere, or are otherwise treated.

Dry dust collector 52 also separates dry particles of alkali metal dihaloisocyanurate from the moist air fed in through dust collector feed line 51. These dry particles are generally too coarse to form hard cohesive granules, particularly if recycled to spray grainer 18. Cohesion of the particles is improved by intensive pulverization. Thus, the dust particles are discharged from dry dust collector 52 through solids discharge line 63 into pulverizor 64. The solid particles are comminuted to a diameter of generally less than about 40 microns and then conveyed through pulverized particle line 65 to solids recycle line 66 which recycles the pulverized solids to spray grainer 18. If desired, a portion or all of the pulverized solids may be recycled to slurry mixer 14 through mixer recycle line 67.

If desired, a portion of the solids flowing in inclined trough 40 may be removed before screening and conveyed through recycle by-pass line 122 to spray grainer 18 through solids recycle line 66 or to make-up slurry mixer 14 through mixer recycle line 67. In addition, a portion or all of the solids from inclined trough 40 may be conveyed through dryer by-pass line 123 to product conduit 48.

The product fraction of rounded granular alkali metal dihaloisocyanurate particles which do not pass through undersize screen 43 and/or particles conveyed from inclined trough 40 to dryer by-pass line 123 are conveyed through product conduit 48 to either product storage conduit 124 or to rotary dryer 68 by means of dryer feed conduit 69. Generally, the water content of the solids in product conduit 48, including the product fraction of screens 41, or dryer by-pass line 123 ranges from about 15 to about 30 percent, and preferably from about 20 to about 25 percent by weight. Generally, these solids have a particle size diameter in the range from about 4 to about 60 mesh, and an available chlorine content in the range from about 60 to about 65 percent by weight on a dry basis, when producing sodium dichloroisocyanurate.

Alkali metal dichloroisocyanurate particles having a moisture content within the above identified ranges, are predominately in the dihydrate form, but may also be admixed with the monohydrate form. From the standpoint of stability, it is preferred that the particles contain at least about 8 percent water in the hydrate form. However, from a standpoint of economic operation of spray grainer 18, it is preferred to heat the particles to a water content of no less than about 15 percent water, since further heating in spray grainer 18 causes a breakdown in the particle size and a large quantity of finely-divided particles are formed. As a result, additional drying to a level below about 15 percent water is done in a separate drying apparatus, such as rotary dryer 68. If the product of spray grainer 18 does not require further drying, the particles from product conduit 48 are conveyed to storage through storage conduit 124.

Rotary dryer 68 is provided with at least two dryer tires 70, preferably constructed of metal, positioned at two mechanically-suitable locations near the extremity of rotary dryer 68. Dryer tires 70 rotate in dryer tire trunnions 71 and rotary dryer 68 is rotated by a suitable dryer motor drive means 72 which acts upon one of the dryer tires 70 to effect rotation of rotary dryer 68.

Rotary dryer 68 is provided with a dryer feed end 73 and a dryer discharge end 74. Dryer feed end 73 is provided with a retaining flange 75 and dryer discharge end 74 is provided with a discharge retaining flange 76 in order to maintain a moving bed of solids in rotary dryer 68. Retaining flange 75 and discharge retaining flange 76 are each provided with a circular opening in the center to permit entrance and exit of particles being dried. Heated air is fed into feed end 73 of rotary dryer 68 through heated air conduit 77. The heated air is provided by blowing atmospheric air through dryer blower 78 into heat exchanger 79 which is heated by exchange with steam fed to steam inlet 80. The heated air is conveyed to heated air conduit 77. The steam condensate is discharged from heat exchanger 79 through condensate discharge line 81.

Figure 3:
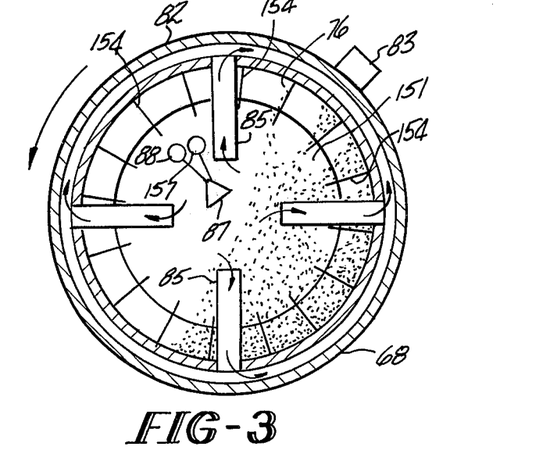
FIG. 3 is a cross-sectional view of the dryer of FIG. 1 through the lines 3—3 of FIG. 1.

FIG. 3 is a cross-sectional view of rotary dryer 68 through 3—3 of FIG. 1. As indicated in FIGS. 1 and 3, rotary dryer 68 is provided with an air exhaust bustle 82 which communicates by means of gas discharge conduit 83 with a dust collection system such as the same type as dust collector 52, exhaust fan 49, and scrubber 54 employed with spray grainer 18. The hot gases which have increased in moisture content within rotary dryer 68 as well as cool air or other inert gas which is drawn into discharge end 74 of rotary dryer 68 through cool gas feed line 84 are withdrawn through tubes 85 located around the periphery of the internal wall of rotary dryer 68. Tubes 85 communicate with a chamber located in bustle 82. Gas discharge conduit 83 positioned in bustle 82 conveys the mixture of gas and any finely divided alkali metal dihaloisocyanurate that may be present in the chamber within bustle 82 to recycle in a separate or the same dust recovery system of the type described above. FIG. 3 also shows retention of the moving bed of solids in dryer 68 by means of discharge flange 76. Granular alkali metal dihaloisocyanurate particles which have been dried in dryer 68 pass over discharge retaining flange 76 into product collection line 86 where they are conveyed to storage or other processing.

If desired, rotary dryer 68 may be provided with a distributing zone 151 having an upper portion 152 and a lower portion 153 in the cooling portion of the drum, preferably in the portion between gas discharge conduit 83 and discharge flange 76. A coating composition such as a low melting inorganic salt may be applied to the dried alkali metal dihaloisocyanurate particles in the distributing zone 151.

Rotary dryer 68 is provided with internal flights 154 in distributing zone 151 similar to lifters 27 of spray grainer 18 in order to maintain a moving bed of alkali metal dihaloisocyanurate particles in lower portion 153. As rotary dryer 68 rotates, a substantial portion of the particles to be coated are lifted to upper portion 152 of rotary dryer 68. As rotation progresses, and the lifted particles approach the top of upper portion 152, the lifted particles are released to fall downwardly through upper portion 152 to the moving bed in lower portion 153. The coating composition is applied as the particles are falling. As a result, there is an increase in the degree of contact between the particles, the coating composition and the cooling air. Little or no dusting occurs. If desired, internal flights 154 may be included in the drying section of rotary dryer 68 to improve contact between the solids and the drying air.

The coating composition is fed to coating composition tank 155 provided with a heater 156, which provides heat to maintain the coating composition at the desired temperature level. The heated coating composition is conveyed by pump 159 through spray feed line 88 to spray nozzle 87 positioned in distribution zone 151. Compressed air is conveyed through compressed air feed line 157 to spray nozzle 87 in order to disperse the coating composition as fine droplets from spray nozzle 87 to effect spraying of these fine droplets of melt onto the falling particles of alkali metal dihaloisocyanurate.

Cool air or other inert gas is fed into discharge end 74 through cooling gas feed line 84. The temperature of the cooling gases is sufficiently low to cool the particles to near ambient temperature. If a coating composition is used, the cooling air also causes solidification of the coating composition on the surface of the particles to improve flowability, prevent caking and form exterior layers of a coating composition which will further protect the encapsulated alkali metal dihaloisocyanurate from ignition when contacted with lighted cigarettes, organic liquids and the like. When the alkali metal dihaloisocyanurate granules are coated in this manner, gas discharge conduit 83 conveys the hot gases containing suspended solids from air exhaust bustle 82 to a separate dry or wet dust collection system (not shown) where solid particles are separated and recycled to the bed or coating composition tank 155 and fed through spray feed line 88 to rotary dryer 68. This technique prevents recycle of the coating composition to the beginning of the process and prevents contamination of the alkali metal dihaloisocyanurate cores with the particles of coating composition.

Bed transport towards the discharge end 74 may be induced by interaction of cascading solids with the co-current flow of drying gases in the drying section of the drum. Rotary dryer 68 may also be set at a positive slope from dryer feed end 73 towards dryer discharge end 74 to aid bed transport to the discharge end. The particles of alkali metal dihaloisocyanurate are thereby moved at a controlled rate from the feed end 73 towards the discharge end 74 as rotary dryer 68 is rotated. Bed depth in discharge end 74 of rotary dryer 68 can be limited by selection of a suitable diameter for retaining flange 76 in discharge end 74.

Although drying, cooling and coating of the alkali metal dihaloisocyanurate particles are preferably accomplished in a single unit as rotary dryer 68, these three steps can be effected in three separate units (not shown) utilizing a rotary dryer or other dryer means to reduce the water content of alkali metal dihaloisocyanurate particles to the desired level, a rotary spray grainer to coat the dried particles with a coating composition, and a rotary cooler to cool the dried particles to a temperature near ambient temperature. The several steps, graining, cooling, drying, and further applications of spray coatings can also be executed sequentially in a single drum in either a batch-wise or continuous operating procedure. The spray grainer is provided with at least one spray nozzle, a plurality of radial lifters, a cooling atmosphere, preferably counter-current to the direction of feed, and means for supplying a coating composition, as described above for the graining end of rotary dryer 68. If the alkali metal dihaloisocyanurate particles to be coated are dry enough when discharged from spray grainer 18, the dryer unit is by-passed and they may be fed directly to the rotary graining unit for coating with the coating composition if such a coating is desired.

More in detail, with respect to the preparation of alkali metal dihaloisocyanurate core particles by the spray graining technique, any pumpable and sprayable alkali metal dihaloisocyanurate slurry containing from about 45 to about 90 percent by weight of water, and preferably from about 55 to about 65 percent by weight of water may be employed. Generally, this slurry is prepared by admixing water or other liquid, if necessary, with the slurry or filter cake of alkali metal dihaloisocyanurate produced in conventional alkali metal dihaloisocyanurate processes of the type described in U.S. Pat. Nos. 3,035,057 and 3,289,319, described above, as well as U.S. Pat. No. 2,913,460, which issued to Arthur G. Brown et al. on Nov. 17, 1959.

Although water is normally used to make up the slurry, any suitable recycle liquid such as a portion of the filtrate produced in commercial alkali metal dihaloisocyanurate, scrubber liquor, or other aqueous medium that is inert to alkali metal dihaloisocyanurate may be employed. If the water concentration of the slurry is below about 45 percent by weight, the resulting slurry is extremely difficult to pump and spray. On the other hand, when the water concentration is above about 90 percent by weight, an extremely large amount of water must be evaporated, and, as a result, the feed rate must be reduced, and the production rate is reduced. In addition, there is excessive decomposition of available chlorine when the moist alkali metal dihaloisocyanurate particles are exposed to the heated atmosphere for the extended periods which are necessary to effect evaporation of such large quantities of water.

The proportion of impurities in the alkali metal dihaloisocyanurate slurry will vary with the type of process employed to prepare the alkali metal dihaloisocyanurate. A typical analysis of a sodium dichloroisocyanurate dihydrate slurry prepared by the reaction of pure aqueous sodium hydroxide, pure cyanuric acid, and pure trichloroisocyanuric acid is:

| Sodium dichloroisocyanurate | 35% by weight |
|---|---|
| Water | 65% by weight |

A typical analysis and a preferred analysis range for the components of the sodium dichloroisocyanurate slurry useful as a starting material in the coating of core particles by the spray graining technique are as follows:

| Compound | Preferred Analysis Range, Percent by Weight | Range, Percent by Weight |
|---|---|---|
| Sodium dichloroisocyanurate | 35–45 | 10–55 |
| Water | 55–65 | 45–90 |

Although sodium dichloroisocyanurate is preferably grained by the process of this invention, other compounds which may be prepared include the corresponding potassium and lithium salts as well as other halogen salts such as the corresponding bromine, fluorine and iodine salts.

A suitable rate of feed of the slurry of alkali metal dihaloisocyanurate particles to spray grainer 18 will depend upon a number of factors such as size of the distribution zone, the relative size of the moving bed, the solids concentration of the slurry, the temperature and velocity of the drying gases, the rate of discharge, and the number of spray nozzles positioned in spray grainer 18. Generally, the slurry feed rate for a slurry containing about 60 percent by weight of water ranges from about 200 to about 500 pounds per hour in a spray grainer 18 having a diameter of about 3 feet. Faster or slower feed rates may be employed, if desired.

The hold-up time in the distribution zones should be maintained at a minimum since excessive exposure of alkali metal dihaloisocyanurate particles to elevated temperature causes a substantial reduction in the available chlorine concentration. Thus, the total hold-up time in the distribution zone generally ranges from about 30 to about 120 minutes and preferably from about 40 to about 60 minutes. Under conditions of restricted heat input, hold-up time may range up to about 90 to about 120 minutes. Hold-up time in rotary dryer 68 or other dryer, when employed, generally ranges from about 5 to about 30 minutes and preferably from about 10 to about 20 minutes. Hold-up time in distributing zone 151, where cooling is effected, may range from about 3 to about 10 minutes, but longer times may be employed, if desired.

The rate of feed or input will have to correspond to the rate of discharge of products in each unit in order to prevent build-up or depletion of the moving bed to an undesirable degree. The number and size of spray nozzles 28 and 87 will depend upon the length of spray grainer 18 or the length of distributing zone 151 in rotary dryer 68, as the case may be. The spray is utilized in order to obtain maximum dispersion and contract of finely divided droplets of the slurry of alkali metal dihaloisocyanurate or coating composition with the moving particles of alkali metal dihaloisocyanurate in the apparatus being employed. In view of the solids content of the aqueous slurry of alkali metal dihaloisocyanurate, it is necessary to use spray nozzles that are provided with openings of sufficient diameter to prevent clogging of the spray nozzles.

The rate of slurry feed through the spray nozzles 28, and 87 must be in balance with the local heat transfer rate in the drum. Since this declines exponentially as the temperature differential declines, the spray rate through two or more sequential nozzles should also be in the same exponential proportion.

In order to obtain the desired dispersion of the alkali metal dihaloisocyanurate slurry in the distribution zone, air, nitrogen, or other suitable gas which is inert to alkali metal dihaloisocyanurate is compressed and used to disperse the aqueous slurry through the spray nozzle heads. In spray grainer 18 of FIG. 1, it is desired to position spray nozzles 28 in upper portion 20 of the distribution zone 19, as indicated in FIG. 2, in the side opposite from the cascading stream of falling particles. The nozzles should be positioned sufficiently close to the falling particles to insure that the slurry contacts the falling particles before the heated gases are capable of evaporating water from the droplets. It is permissable for each spray to be in contact with the cascading stream of falling particles of alkali metal dihaloisocyanurate provided the force of the stream is not strong enough to block the discharge of the spray of alkali metal dihaloisocyanurate slurry from spray nozzles 28.

Generally, the dried alkali metal dihaloisocyanurate particles produced in rotary dryer 68, with or without the application of a protective coating have a particle size which ranges from about 4 mesh to about 60 mesh, and preferably from about 14 mesh to about 30 mesh. The thickness of the protective coating and any additional alkaline inorganic salts, if present, is generally sufficient to comprise from about 4 to about 45 percent by weight, and preferably from about 4 to about 40 percent by weight of the entire alkali metal dihaloisocyanurate granule. The average available chlorine content of the entire alkali metal dichloroisocyanurate granule generally averages from about 50 to about 65 percent and preferably from about 61 to about 63 percent by weight (dry basis). The average water content of the granules ranges from about 1 to about 15 and preferably from about 2 to about 8 percent by weight.

The available chlorine content of pure potassium and lithium dichloroisocyanurate cores generally ranges from about 60 to about 70 percent by weight, respectively. Sodium dichloroisocyanurate cores contain about 64.5 percent by weight available chlorine on a dry basis.

Because of the heterogeneous nature of the exterior layer, the coated alkali metal dihaloisocyanurate particles are more stable to thermal decomposition and loss of available chlorine.

Axial rotation of spray grainer 18, and rotary dryer 68 is preferably within the range from about 45 rpm to about 10 rpm when the diameter of the drum ranges from about 1 foot to about 12 feet. These rotation speeds are determined in accordance with the formula:

$$rpm = 20 \sqrt{3/D(ft.)}, \text{ where } D = \text{drum diameter}$$

Lower speeds are also practical in accordance with the formula:

$$rpm = 5 \sqrt{3/D(ft.)}$$

Other speeds between and beyond these limits are also permissable.

Rotation of spray grainer 18 and rotary dryer 68 is effected by any convenient motor driven means such as electric motors with chain or gear drives.

Evaporation of the liquid component of the slurry is effected in spray grainer 18 by any suitable heating means such as by means of a heated gas such as air or nitrogen or other gas which is inert to alkali metal dihaloisocyanurate. The gas may be heated indirectly in a heat exchanger, with steam, hot combustion gases, or any other suitable manner. Gases which contain relatively large proportions of carbon dioxide and water vapor are not suitable for drying the liquid components from the slurry in spray grainer 18 since the water component and the carbon dioxide component react with the alkali metal dihaloisocyanurate particles to form undesirable by-products. However, combustion gases or other heating means may be used to externally heat spray grainer 18 in order to maintain a temperature within spray grainer 18 which is sufficiently high to effect the removal and evaporation of liquid from the slurry of alkali metal dihaloisocyanurate without excessive decomposition of the resulting solid alkali metal dihaloisocyanurate granules. Other suitable heating means include external heating of the distribution zone with combustion gases, liquid or solid fuels impinging on the drum walls, electrical heat, direct flame or other direct heating source being applied to the exterior of spray grainer 18.

As indicated in FIG. 1, evaporation and removal of water from the slurry on the surface of the alkali metal dihaloisocyanurate core particles is effected by passing a stream of heated gas, such as air, nitrogen or other inert gas co-currently through spray grainer 18. If external means are utilized to heat the distribution zone, it is still necessary to maintain a flow of gas through the distribution zone in order to remove the humidified atmosphere that is formed by evaporation and removal of the water from the slurry on the core particles. The temperature of the distribution zone is maintained in the range from about 40° to about 70° C., and preferably from about 45° to about 60° C., by means of the heated gas which is passed through the distribution zone. It is preferred to pass the air con-current to the flow of the moving bed of solids in spray grainer 18, but counter-current flow may also be employed, if desired. The temperature and volume of the gas feed to the distribution zone are correlated with the rate of feed of the slurry, recycle solids, water content and residence time in order to maintain a suitable bed temperature and also effect the desired degree of evaporation of moisture from the alkali metal dihaloisocyanurate particles. In order to maintain the temperature of the distribution zone within the above defined ranges, it is generally necessary to feed heated gas into the feed end of spray grainer 18 at a temperature in the range from about 75° C. to about 250° C., and preferably from about 100° C. to about 200° C. The higher temperatures are suitable with short residence times and higher bed temperatures and the lower temperatures are employed with the longer residence times at lower bed temperatures in order to minimize excessive decomposition of the available chlorine component of the alkali metal dihaloisocyanurate particles due to overheating.

As indicated in FIG. 1, it is preferred to screen or otherwise classify the product of spray grainer 18 to obtain a product fraction of the desired particle size. However, if particle size of the product is not important, sizing of the product of spray grainer 18 can be eliminated. In that case, seed particles of finely divided alkali metal dihaloisocyanurate from another source are fed to spray grainer 18 for for coating with alkali metal dihaloisocyanurate. Generally, the product fraction ranges from about 4 to about 60 mesh and preferably from about 14 to about 30 mesh.

In a preferred embodiment of the invention, the product of spray grainer 18 which is predominantly in the dihydrate form, is screened to obtain a product fraction within the above defined particle size range, and then further dried to a water content in the range from about 1 to about 15 percent, and preferably from about 1 percent to about 8 percent by weight of water. Drying to remove this much water of hydration is generally effected in a dryer such as rotary dryer 68 at a temperature in the range from about 70° C. to about 110° C., and preferably from about 75° C. to about 105° C. In order to maintain this drying bed temperature, heated air or other suitable gas is fed to the dryer con-currently with the feed at a temperature in the range from about 75° C. to about 250° C. Simultaneously, ambient cooling air having a temperature from about 20° C. to about 40° C., for example, is fed counter-currently at the discharge end of dryer 68 in order to reduce the temperature of the dried coated particles to within a range where decomposition of the available chlorine component of the alkali metal dihaloisocyanurate particles does not occur to a substantial degree. This technique reduces decomposition and also avoids problems of aggregation and sticking of the finished rounded smooth coated alkali metal dihaloisocyanurate product. The coated product can also be conveyed to a separate air-cooled cooling drum, to conveyor coolers with water cooled jackets, to fluidized bed air coolers or the like for further cooling, if desired. Storage of the cooled coated particles is done after cooling the particles to below about 40° C.

Drying of the coated alkali metal dihaloisocyanurate in rotary dryer 68 is generally a dehydration step as well as a drying step. Solid alkali metal dihaloisocyanurate particles in the aqueous slurry fed to spray grainer 18 are primarily in the form of alkali metal dihaloisocyanurate dihydrate which contains about 14.1 percent by weight of hydrated water. Thus, when the product fraction discharged from product conduit 48 contains more than about 14.1 percent water by weight, the water in excess of this amount is free water. When the product from product conduit 48, or the dry product in rotary dryer 68 before coating with the protective coating contains less than about 14.1 percent water, the bulk of the water is present as hydrated alkali metal dihaloisocyanurate rather than as free water.

The alkali metal dihaloisocyanurate particles produced by this novel process are ready for packaging, storage, shipping and use in the purification of water and the like.

In addition to producing coating alkali metal dihaloisocyanurate particles of improved strength and stability, the spray graining technique for preparing the alkali metal dihaloisocyanurate particles of this invention also results in improved yield of alkali metal dihaloisocyanurate based upon initial reactants, since there is a substantial reduction in the amount of available chlorine lost during the processing of the filter cake to produce a dry coated granular product.

Conventional granular alkali metal dihaloisocyanurate particles are in the form of irregular sharp-edged flakes which must be prepared and dried under substantially quiescent conditions with a minimum of agitation because of the sensitivity of the fragile edges to attrition and a high level of dusting. Unlike conventional granular alkali metal dihaloisocyanurate, the rounded granular coated alkali metal dihaloisocyanurate particles of this invention can be subjected to severe conditions of agitation and crushing during granulation and drying without the formation of excessive quantities of dust because sharp, fragile edges are totally absent.

Without being bound by theory, it is believed that the improved structure of the coated alkali metal dihaloisocyanurate particles of this invention are a result of the formation of pliable molten layers of alkali metal dihaloisocyanurate solids by the spray graining technique which are packed and pounded onto the dried hardened underlaying core or seed substrate by innumerable impacts as the particles cascade in the distribution zone or are otherwise forced into violent collision with one another during processing.

As the solid progress through the distribution zone, layer upon layer of alkali metal dihaloisocyanurate are formed in spray grainer 18 in an onion skin-like manner. If a coating composition is added in rotary dryer 68 to the alkali metal dihaloisocyanurate particles, then layer upon layer of the coating composition is formed in an onion skin-like manner, each layer also imparting strength to the particles.

The novel coated granules of this invention have a high degree of integrity and when subjected to severe pressing force will fracture into integral particles of the granule, rather than decompose into dust, which occurs with conventional granular alkali metal dihaloisocyanurte particles under the same conditions.

The term "rounded" used to characterize the novel alkali metal dihaloisocyanurate particles of this invention is intended to cover particles which are substantially spherical in shape, but which may exhibit "egg-shaped" distortion also. Irregular particles have a maximum diameter and a minimum diameter. The ratio of the maximum diameter to the minimum diameter of irregular particles of alkali metal dihaloisocyanurate produced in conventional commercial processes is generally greater than about 2:1. In contrast, the novel alkali metal dihaloisocyanurate particles of this invention approach a spherical shape and generally have a ratio of maximum diameter to minimum diameter of about 1.5:1 or less, particularly when the core is prepared by the spray graining technique.

A further difference between the novel rounded particles of this invention and the irregular shaped conventional particles is that the outer surface of the rounded particles of this invention is a substantially smooth undisturbed layer of alkali metal dihaloisocyanurate or coating composition which is formed. In contrast, the irregular shaped alkali metal dihaloisocyanurate particles of commerce have been formed by compressing wet filter cake between compression rollers to form a sheet-like material, and then fracturing the sheet into irregular shaped platlets which are subsequently dried under quiescient conditions. Because of the unique procedure for preparing the novel coated compositions of of this invention, there is a markedly improved resistance to dusting and physical and chemical breakdown.

The following examples are presented to define the invention more clearly without any intention of being limited thereby. All parts and percentages are by weight unless otherwise specified.

EXAMPLE 1

A rotary spray grainer was constructed of a drum 12 inches in diameter, 12 inches long and adapted to rotate at a speed of about 36 rpm. 12 1-inch radials were secured at points approximately equi-distant around the interior wall. Access to the interior of the drum was through a 4 inch opening at one end. The drum axis was horizontal and the drum speed was sufficient to produce cascading of the bed of solid particles over about 50 percent of the cross sectional area of the drum.

Finely divided particles of anhydrous sodium dichloroisocyanurate were wetted with water to form a stiff paste, wherein the ratio of powder to water was approximately 50 parts of powder to 25 parts of water. The resulting stiff paste was crushed into grains having a particle size of approximately −4+40 mesh. The resulting wet grains were kneaded and broken up to −12 mesh granules. The particles were heated in the rotating drum while applying a continuous flame of a blast burner to the outside of the drum to cause drying of the particles in the bed to approximately the dihydrate state. This portion of dried granular product was used as a seed bed subsequently to be coated with a sprayable slurry of sodium dichloroisocyanurate.

A slurry of sodium dichloroisocyanurate dihydrate was prepared by admixing approximately 400 parts of powder with about 1000 parts of water. The resulting slurry was sprayed in 10 milliliter increments into the rotating drum onto the cascading bed of dry particles. Approximately 2 hours were required to feed 800 grams of powder as a slurry of the above defined concentration. The temperature of the bed and the drum interior was maintained about 40° C.

The resulting particles of sodium dichloroisocyanurate dihydrate were substantially dust-free, and thus virtually no breakdown was caused by attrition during the process.

The resulting bed of sodium dichloroisocyanurate dihydrate was heated in the rotating drum, employing a gradual temperature rise. The variation of time and temperature were as follows:

| Time of Heating, Minutes | Temperature, ° C. |
|---|---|
| 5 | 70 |
| 8 | 75 |
| 10 | 79 |
| 12 | 83 |
| 14 | 100 |
| 15 | 105 |
| 20 | 105 |
| 23 | 107 |
| 25 | 109 |
| 26 | 110 |
| 30 | 75 |
| 35 | 45 |

Loss of available chlorine during the spray graining operation was 0.3 percent by weight. Slight dust formation due to abrasion of the grain occured above temperatures of about 70° C. The resulting grains, however, were hard and firm. Screen analysis of the resulting bed of anhydrous sodium dichloroisocyanurate was as follows:

| Mesh Size | Weight in Grams | Percentage |
|---|---|---|
| −8+12 | 145 | 9.6 |
| −12+16 | 295 | 19.4 |
| −16+20 | 273 | 18.0 |
| −20+30 | 330 | 21.7 |
| −30+40 | 380 | 25.0 |
| −40 | 95 | 6.3 |

Thus, it can be seen that substantially few fines (6.3 percent) were formed during the graining operation.

EXAMPLE 2

A slurry of sodium dichloroisocyanurate was made by digesting trichloroisocyanurate, sodium hydroxide and cyanuric acid according to the following reaction:

$$3NaOH + 2C_3N_3Cl_3 + C_3H_3N_3O_3 \rightarrow 3C_3NaN_3Cl_2 + 3H_2O$$

water entering the reaction with the NaOH sufficed to yield a pumpable and sprayable slurry containing 35% sodium dichloroisocyanurate and 65% percent water.

The slurry was sprayed onto a seed bed in a drum 3 feet in diameter and 6 feet long rotating at 20 rpm. Attached to the inner periphery of the drum were 24 radial flights one inch in height. The seed ranged in size from 24 mesh to 40 mesh. The weight of the seed bed was 150 pounds. Air heated to 180° C. was conducted co-currently through the drum at the rate of 1250 cubic feet per minute. Slurry was sprayed onto the seed bed at the rate of 6 pounds per minute. Evaporation of water resulted in the deposition of 2.5 pounds per minute of dry sodium dichloroisocyanurate dihydrate with the seed thereby also inducing the growth of the seed grain. Bed moisture was 20% with a bed temperature of 50° C.

Co-current air flow induced bed transport from the feed end of the drum to the discharge end at the rate of 50 pounds per minute. An external conveyor was provided to recycle the transported bed to the feed end of the drum. A fraction of the recycle stream was screened to remove product grain in the range 14 to 20 mesh from the recycled bed. Plus 14 mesh oversize was also isolated as it formed, crushed to a minus 30 mesh size and returned to the bed. The rate of product grain isolation was maintained at 2.5 pound-per-minute rate to stabilize the bed weight at 150 pounds. Operation was continued over a period of 4 hours to produce 550 pounds of grained product having a screen analysis as follows:

| Screen Size U.S. Sieve Series | Percentage |
|---|---|
| −14 +18 | 25 |
| −18 +24 | 35 |
| −24 +30 | 20 |
| −30 +40 | 15 |
| −40 | 5 |
| | 100 |

EXAMPLE 3

Product from Example 2 containing 20% moisture in the amount of 250 pounds was loaded into a drum 3 feet in diameter and 6 feet long fitted with 24 radial flights 1 inch high and turning at 20 rpm. Bed transported out of the discharge end of the drum by co-current air flow was returned to the feed end via an external recycle conveyor. Air heated to 200° C. was introduced co-currently at the rate of 900 cubic feed per minute. Temperatures at 5 minute intervals are as tabulated below:

| Time, Minute | Temperature, ° C. |
|---|---|
| 0 | 30 |
| 5 | 70 |
| 10 | 75 |
| 15 | 100 |
| 20 | 105 |
| 25 | 110 |

Drying was stopped as the bed temperature reached 110° C. Residual moisture in the product was 0.9%. Residual moisture in a sample of product taken after 10 minutes of drying (bed temperature 75° C.) was 8.5%. The weight of dried bed recovered was 200 pounds. Since the weight of moisture volatilized was 48 pounds, the calculated dust amounts to 2 pounds or about 1% of the bed weight. In a parallel test where crushed sodium dichloroisocyanurate with sharp edges was tumbled for 25 minutes in the same drum, the weight of recovered product was only 95% of the starting bed. Calculated dust loss by attrition of sharp edges was therefore 5%.

What is claimed is:

1. Granular particles of alkali metal dihaloisocyanurate each having a smooth rounded surface comprised of a core of alkali metal dihaloisocyanurate encapsulated with a plurality of individual coating layers of hydrated alkali metal dihaloisocyanurate, wherein said core ranges in diameter from about 200 to about 2000 microns and the outside diameter of said particles ranges from about 400 to about 5000 microns.

2. The particles of claim 1 wherein said individual layers are formed of an alkali metal dihaloisocyanurate dihydrate.

3. The particles of claim 2 wherein the water content ranges from about 1 to about 15 percent by weight.

4. The particles of claim 3 wherein each particle is comprised of a core of anhydrous alkali metal dihaloisocyanurate encapsulated with a plurality of layers of hydrated alkali metal dihaloisocyanurate.

5. The particles of claim 4 wherein said alkali metal dihaloisocyanurate is sodium dichloroisocyanurate.

6. The particles of claim 3 wherein said core and said individual layers are comprised of alkali metal dihaloisocyanurate dihydrate.

7. The particles of claim 6 wherein said alkali metal dihaloisocyanurate is sodium dichloroisocyanurate.

8. The particles of claim 3 wherein the particle size of said alkali metal dihaloisocyanurate particles ranges from about 14 mesh to about 30 mesh.

9. The particles of claim 8 wherein the water content of said particles ranges from about 1 to about 8 percent by weight.

10. The particles of claim 9 wherein said alkali metal dihaloisocyanurate is an alkali metal dichloroisocyanurate.

11. The particles of claim 10 wherein said alkali metal dihaloisocyanurate is sodium dichloroisocyanurate.

12. The particles of claim 10 wherein said alkali metal dihaloisocyanurate is potassium dichloroisocyanurate.

13. The particles of claim 10 wherein said alkali metal dihaloisocyanurate is lithium dichloroisocyanurate.

14. A method for preparing particulate solid alkali metal dihaloisocyanurate having a smooth rounded surface from a pumpable and sprayable aqueous slurry of alkali metal dihaloisocyanurate dihydrate which comprises:

a. maintaining a moving bed of particulate solid alkali metal dihaloisocyanurate dihydrate in the lower part of a distributing zone having an upper part and a lower part, b. lifting a portion of said moving bed to said upper part and releasing said particles to separately fall through said distributing zone to said bed, c. spraying on said falling particles a pumpable and sprayable aqueous slurry of alkali metal dihaloisocyanurate, d. maintaining a temperature in said distribution zone sufficiently high to simultaneously evaporate and remove water from said slurry on said falling particles, whereby the resulting particles after water removal are coated with a layer of solid alkali metal dihaloisocyanurate hydrate, and e. removing at least a portion of the resulting coated rounded solid hydrated alkali metal dihaloisocyanurate particles from said distributing zone.

15. The method of claim 14 wherein said slurry contains from about 45 to about 90 percent by weight of water.

16. The method of claim 15 wherein said particles contain from about 15 to about 30 percent by weight of water.

17. The method of claim 16 wherein said temperature in said distributing zone is from about 40° to about 70° C.

18. The method of claim 14 wherein said coated solid alkali metal dihaloisocyanurate particles removed from said distributing zone are heated in a separate drying zone to further remove water therefrom.

19. The method of claim 18 wherein said further dried coated solid alkali metal dihaloisocyanurate particles contain from about 85 to about 99 percent alkali metal dihaloisocyanurate by weight and from about 1 to about 15 percent by weight of water.

20. The method of claim 19 wherein a temperature of said drying zone is from about 70° C. to about 110° C.

21. The method of claim 17 wherein at least a portion of said particles removed from said distributing zone is classified into a product fraction, an over-size fraction and an under-size fraction, said under-size fraction is returned to said distributing zone, said over-size fraction is crushed and reclassified, and said product fraction is recovered.

22. The method of claim 18 wherein said particles in said drying zone are heated by passing a stream of gas inert to alkali metal dihaloisocyanurate through said drying zone, said drying zone being maintained at a temperature in the range from about 75° to about 250° C.

23. The method of claim 22 wherein the particles of said particulate product have a core of solid anhydrous alkali metal dihaloisocyanurate coated with a shell of solid alkali metal dihaloisocyanurate dihydrate.

24. The method of claim 22 wherein said alkali metal dihaloisocyanurate is sodium dichloroisocyanurate.

25. The method of claim 22 wherein the particles of said particulate product have a core of hydrated alkali metal dihaloisocyanurate and are coated with a shell of solid alkali metal dihaloisocyanurate dihydrate.

26. The method of claim 25 wherein said alkali metal dihaloisocyanurate is sodium dichloroisocyanurate.

* * * * *